United States Patent [19]

Hach

[11] Patent Number: 4,645,745
[45] Date of Patent: Feb. 24, 1987

[54] DIGESTION PROCESS

[75] Inventor: Clifford C. Hach, Loveland, Colo.

[73] Assignee: Hach Company, Loveland, Colo.

[21] Appl. No.: 807,537

[22] Filed: Dec. 12, 1985

Related U.S. Application Data

[63] Continuation-in-part of Ser. No. 583,984, Feb. 27, 1984, abandoned.

[51] Int. Cl.$^4$ ......................... G01N 1/28; G01N 33/00
[52] U.S. Cl. .................................... 436/114; 436/115; 436/175
[58] Field of Search ............... 436/111, 113, 114, 115, 436/149, 150, 151, 155, 157, 163, 164, 175, 179

[56] References Cited

U.S. PATENT DOCUMENTS

| | | | |
|---|---|---|---|
| 2,644,743 | 7/1953 | Clevenger et al. | 422/104 |
| 3,450,501 | 6/1969 | Oberhardt | 436/69 X |
| 3,494,201 | 2/1970 | Roach | 422/100 X |
| 4,080,168 | 3/1978 | Abu-Samra et al. | 436/175 |
| 4,081,345 | 3/1978 | Tolg et al. | 436/149 X |
| 4,229,180 | 10/1980 | Christoffersen et al. | 436/114 |
| 4,347,216 | 8/1982 | Kawasaki et al. | 422/80 X |

FOREIGN PATENT DOCUMENTS

| | | | |
|---|---|---|---|
| 0011200 | 4/1973 | Japan | 436/113 |
| 0049085 | 4/1977 | Japan | 436/175 |
| 0143341 | 5/1920 | United Kingdom | 436/113 |
| 0292099 | 1/1971 | U.S.S.R. | 436/114 |

OTHER PUBLICATIONS

Krishnamurty et al., Atomic Absorption Newsletter, vol. 15, No. 3, pp. 68-70, 1976.
Razumov et al., Chemical Abstracts, vol. 96, Abstract No. 96:19370w, 1981.
Lowther, Chemical Abstracts, vol. 92, Abstract No. 92:211204g, 1980.
Kuznetsova et al., Industrial Laboratory (U.S.A.), vol. 42, No. 2, p. 207, 1976.
Ogg, Journal of the A.O.A.C., vol. 43, No. 3, pp. 689-693, 1960.
Bradstreet, "The Kjeldahl Method of Organic Nitrogen", *Academic Press*, New York, 1965.
Miller et al., Anal. Chem., vol. 20, No. 5, pp. 481-488, 1948.
Lake et al., Anal. Chem., vol. 23, No. 11, pp. 1634-1638, 1951.
McKenzie et al., Australian J. Chem., vol. 7, pp. 55-70, 1954.
Shirley et al., Ind. Eng. Chem., vol. 17, No. 7, pp. 437-438, 1945.

*Primary Examiner*—Barry S. Richman
*Assistant Examiner*—Robert J. Hill, Jr.
*Attorney, Agent, or Firm*—Dean P. Edmundson

[57] ABSTRACT

An improved process for quantitatively determining nitrogen content in a wide variety of materials. The process avoids the use of conventional catalysts, is simpler and faster than previous techniques, and results in a very high degree of accuracy. The process involves the use of a reagent solution prepared by mixing hydrogen peroxide and concentrated sulfuric acid. The digestion process also enables quantitative determination of various elements other than nitrogen.

19 Claims, 3 Drawing Figures

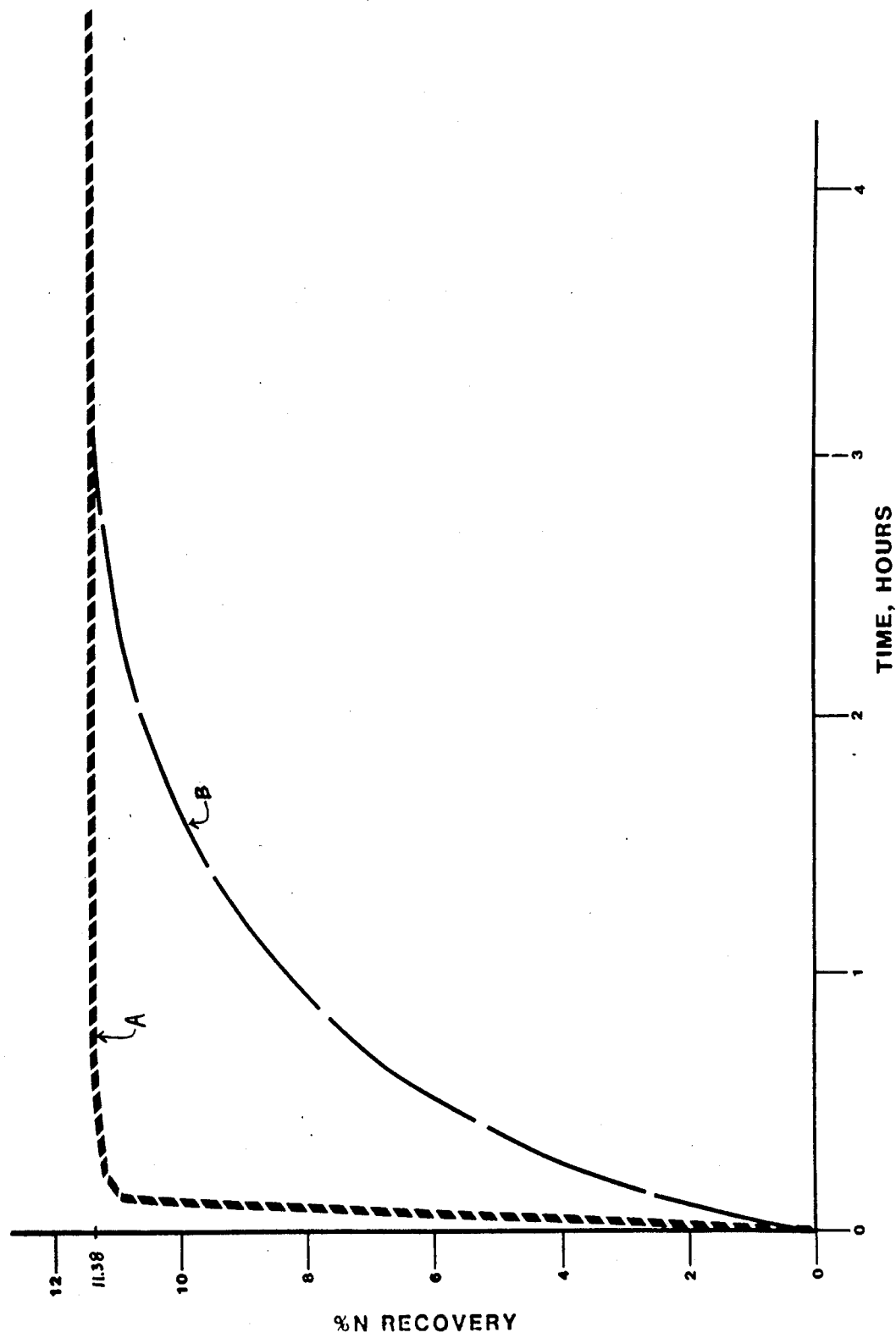

DIGESTION PROCESS

CROSS-REFERENCE TO RELATED APPLICATION

This application is a continuation-in-part of my copending application Ser. No. 06/583,984, filed Feb. 27, 1984, now abandoned.

FIELD OF THE INVENTION

This invention relates to digestion processes. More particularly, this invention relates to processes for quantitative determination of nitrogen and other elements in various substances.

BACKGROUND OF THE INVENTION

The need to quantitatively determine the amount of nitrogen and other elements contained in various organic compounds has been widespread for more than one hundred years. The need for determining the amount of nitrogen present led Johann Kjeldahl of Denmark to develop a method involving heating the substance in concentrated sulfuric acid and then adding powdered potassium permanganate. After addition of the permanganate the solution was diluted, transferred to a distilling flask, made alkaline, zinc added, and then distilled into standard acid. Potassium iodide and iodate were added to the distillate, and the liberated iodine was titrated with standard thiosulfate. See *The Kjeldahl Method for Organic Nitrogen*, R. B. Bradstreet (1965).

Others later learned that the speed of reaction in concentrated sulfuric acid was accelerated by the use of catalysts, such as the oxides of iron, mercury, manganese, bismuth, zinc, lead, and copper. Selenium was also touted as a good catalyst in the method, as was selenium dioxide-mercuric sulfate (1:1) and selenium dioxide-copper sulfate (3:1).

Because Kjeldahl's method required a considerable amount of time to digest the substance being tested, there was a desire to shorten the digestion time. This was eventually made possible when it was discovered that the addition of potassium sulfate raised the boiling point of the digestion mixture. Later it was found that the addition of various other sulfates and phosphates were also effective in raising the boiling point.

Hydrogen peroxide is reported to have been used in the Kjeldahl method as an oxidizing agent but with only limited success in aiding the digestion process. One researcher recommended the use of 30% hydrogen peroxide by mixing it with the organic matter to be treated, after which concentrated sulfuric acid is added slowly with shaking. Then potassium sulfate is added, and the mixture is then boiled. Modifications of the method by others involved adding various co-catalysts.

In another variation it was suggested to successively add 1–5 drops of 30% hydrogen peroxide to the carbonized digest, heat the digest until fumes appear, and reheat the digest after each addition. In yet another variation it was suggested to add peroxide after first heating the digest for five minutes over low flame. Then additional acid, copper sulfate catalyst and potassium sulfate are added and the resulting mixture heated until fumes are given off. Peroxide is then added until the solution remains blue and the digest is then heated for an hour with a high flame. Another suggested adding bromine after the organic matter has charred, reheating the digest, and again adding bromine with several drops of hydrogen peroxide; later peroxide is added alone.

It has also been suggested to heat the organic matter with oleum, then cool the digest after charring, followed by addition of peroxide to the cold digest. The digest is then heated for five minutes and the procedure repeated.

In yet another procedure concentrated sulfuric acid is added to the sample of organic matter and then allowed to stand for 15 minutes at room temperature before heating for several minutes. After cooling the digest, there are added 10–20 ml. of peroxide in small portions so as to avoid a large evolution of gas. After heating to expel the gas, the digest is boiled for five minutes and then the procedure is repeated until a clear solution results.

The various complexities and problems associated with the use of oxidizing agents in the Kjeldahl process have led researchers to conclude that it is better to depend upon the higher temperatures obtained by salt addition and an accelerated reaction rate through the use of catalysts than upon the use of an oxidizing agent to promote oxidation of organic matter. See p. 42 of *The Kjeldahl Method for Organic Nitrogen*, supra. The use of hydrogen peroxide has not been very satisfactory because of the time consuming, tedious nature of its application and only partial success in improving the Kjeldahl method. None of the previous methods using hydrogen peroxide have been proven to be faster or more accurate than other conventional Kjeldahl methods.

In the prior methods which utilized peroxide or peroxysulfuric acid, the concentration of the peroxide or peroxysulfuric acid was not maintained for sufficient time at a sufficiently high temperature to obtain any significant oxidation. The addition of hydrogen peroxide solution alone to hot sulfuric acid results in a violent decomposition at the surface of the acid layer with little benefit toward oxidation of the organic material dissolved in the sulfuric acid.

In U.S. Pat. No. 4,229,180 (Christofferson) there is described a process for determining nitrogen in a sample, according to the Kjeldahl principle, in which an antimonate compound is used as a catalyst. Mention is made at Column 2 that the antimonate may be added as a powder, granulate, tablet, or as a solution in water or in a component which is to be added in the destruction anyway, such as hydrogen peroxide or sulfuric acid or mixtures thereof. Such patent does not describe predigesting the sample in sulfuric acid. Apparently the hydrogen peroxide is added, with concentrated sulfuric acid, to the sample along with the catalyst and salt (for increasing the boiling point) before the sample is heated. Then the destruction mixture is heated to 400° C. to 410° C., during which water and peroxide are evaporated or consumed.

Unfortunately, when the digest is heated at 410° C. or more there is a loss of nitrogen from the digest. As a result, the quantitative determination of nitrogen in the final digest will be erroneous. Also, when various salts are added to the digest in order to increase the boiling point of the sulfuric acid, such salts remain in the digest and prevent the digest from being used for quantitative determinations of elements (such as potassium) which are present in the added salts. Of course, the presence of catalyst has the same effect. Christofferson's method, using both catalysts and salts, requires temperatures and digestion times well outside that required in the process of the present invention (which does not use either catalysts or salts).

Yet another procedure is described in Analytical Chemistry, 20, pp. 481–488 (1948) in which the material sample is digested in sulfuric acid for five minutes, then cooled, after which two drops of hydrogen peroxide are added. Then the digest is heated again for two minutes and then cooled, after which another two drops of hydrogen peroxide are added. This process may be repeated several times. The process is tedious and time-consuming. The digestion time required for complete nitrogen recovery using such a process is several times longer than that obtainable by the process of the present invention.

Possibly the most advanced study of the use of peroxide is described in Australian J. Chem., 7, pp. 55–70 (1954) which reported only partial success, with difficulty, in using peroxide. The article reports that a fifty-minute digestion (with sulfuric acid and peroxide) of the amino acid tryptophan resulted in only 98.3% recovery of nitrogen, and that digestion included ten separate additions of peroxide.

As stated in Analytical Chemistry, Vol. 23, No. 11, p. 1634 (1951), the temperature attained in digestion of the sample in the Kjeldahl procedure has been of prime importance. Too low a temperature either requires too long a digestion time or fails to give good results. Too high a temperature may result in loss of nitrogen from the digest. For samples containing nitrogen in pyridine ring structures, digestion at temperatures below 370° C. did not give quantitative recovery of pyridine with one hour digestion. At temperatures above 410° C. it was reported that nitrogen may be lost.

In Industrial and Engineering Chemistry, Vol. 17, pp. 437–8 (1945) it was reported that a digestion time of 2–4 hours was required for compounds such as pyridine, nicotine and nicotinic acid, using various types of catalysts.

In the Official Methods of Analysis of the Association of Official Analytical Chemists, the most commonly-used official method, it is recommended that any sample containing organic material be digested for at least two hours.

Such prior procedures are very undesirable for many situations, particularly where very accurate results are required or where time is of the essence in obtaining the results. Also, prior procedures are cumbersome or tedious. As a result, the person conducting the testing must follow the prescribed procedure carefully to avoid mistakes.

There has not heretofore been provided a technique for the rapid and accurate digestion of samples which produces a digest suitable for determination of nitrogen and for other elements also.

SUMMARY OF THE PRESENT INVENTION

In accordance with the present invention there is provided a simple and efficient process for the quantitative determination of nitrogen content and various other elemental content in various substances such as, for example, food products, animal feeds, grains, plant and animal tissue, fertilizers, protein, petroleum, coal, urea, amino acids, organic compounds including amines, amides, azo compounds, heterocyclic ring compounds such as pyridine and porphines.

The new process includes the steps of:
(a) placing a weighed sample of the material to be tested in a digestion flask;
(b) adding concentrated sulfuric acid to the flask to form a digest;
(c) heating the digest at a temperature and for a time sufficient to char the sample and bring the sulfuric acid to a boil at a temperature less than about 330° C.;
(d) continuously adding to the digest, while said digest is boiling, a reagent solution prepared by mixing hydrogen peroxide and concentrated sulfuric acid;
(e) heating the digest at a temperature less than about 330° C. for a time sufficient to convert nitrogen present in the sample to ammonium ion said time being less than about 15 minutes;
(f) optionally, cooling the digest;
(g) optionally, diluting the digest with water to form a test solution; and
(h) quantitatively determining the nitrogen content, or other desired elemental content, from the test solution.

The process of the invention is much simpler and faster than previous techniques. Yet the process results in a very high degree of accuracy for nitrogen analysis and is more accurate than many commercially utilized techniques. Moreover, the process does not require the use of any catalysts, and it does not consume a large amount of reagent. Since an aspirator is sufficient to remove fumes during digestion, there is no need to use a fume hood during the process. The process enables accurate nitrogen determinations on compounds often considered refractory when tested according to the traditional Kjeldahl method. Complete recovery of nitrogen in typical food and feeds can be accomplished after five minutes of digestion time, while difficult compounds such as lysine, pyridine and nicotinic acid require less than about 15 minutes of digestion time. This is an increase in speed of digestion of about five-to-ten fold over previous methods and is an unexpected improvement over previous methods.

Still another significant advantage is that the resulting digest is also suitable for various chemical determinations other than nitrogen.

Because the temperature of the digest is maintained at a very low level (i.e., in the range of about 240° C. to 330° C.) there is no loss of nitrogen or other desired element during the digestion process and the digest is safer to handle. Yet, surprisingly, the nitrogen in the sample is rapidly and completely converted to ammonium ion so that its presence can be quantitatively determined easily and with a very high degree of accuracy.

BRIEF DESCRIPTION OF THE DRAWINGS

The invention is described in more detail hereinafter with reference to the accompanying drawings, wherein like reference characters refer to the same parts throughout the several views and in which:

FIG. 3 is a graph illustrating the speed and accuracy of the process of this invention.

DETAILED DESCRIPTION OF THE INVENTION

Figure 1:
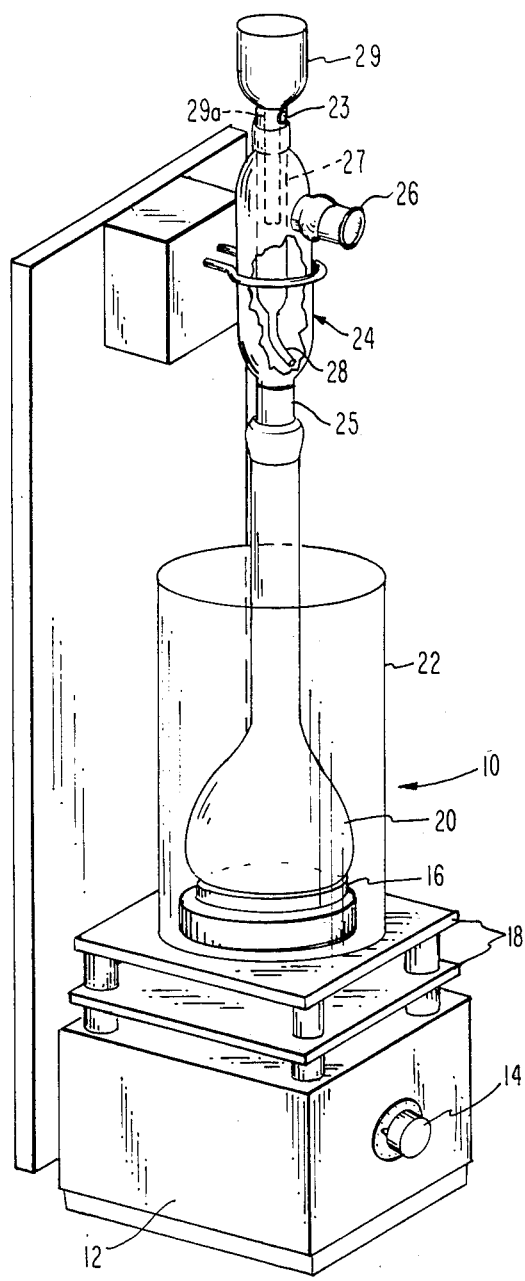
FIG. 1 shows one embodiment of apparatus which is useful in the practice of the present invention.

Thus, in FIG. 1 there is shown one embodiment of digestion apparatus 10 which is useful in the practice of this invention. The apparatus includes conventional electrical resistance heater assembly 12 which may be controlled as to temperature by means of control switch 14. The heated platen 16 is separated from the heater housing by means of asbestos layers 18.

Volumetric flask 20 is adapted to rest on the top of heated platen 16, as shown. Preferably a heat resistant glass chimney 22 surrounds the flask as a safety measure (i.e, to prevent the flask from being inadvertently bumped off the heated platen). A convenient size for the volumetric flask in the techniques of the present invention is 100 milliliters.

Mounted at the top of the volumetric flask is a manifold 24 which includes lower end 25 which is adapted to fit into the open top end of the flask. Side fitting 26 communicates with the open chamber in manifold 24 and is adapted to be attached to a conventional aspirator. Contained within manifold 24, and secured thereto, is funnel or conduit 27 which includes a lower exit tube 28. Fluid may be introduced into funnel 27 through capillary funnel 29 which sits on top of manifold 24, as shown in FIG. 1. The fluid exits funnel 29 at a slow, controlled, uniform rate through the lower end of capillary tube 29a and into funnel 27. Preferably the lower end 28 of funnel 27 is disposed such that the exit fluid flows along the interior surface of the manifold 24 and thence along the interior surface of the volumetric flask. Consequently, fluid which is fed to the digestion flask through manifold 24 will interface and mix with the digest at an interior surface of the flask.

Fumes generated during the digestion process are drawn off through the manifold and out side fitting 26 to the aspirator. This avoids the need for an exhaust hood to contain the apparatus during the process.

Aperture 23 in the side of manifold 24 enables room temperature air to enter and surround capillary tube 29a. This maintains tube 29a at or near room temperature and, accordingly, the flow rate of the fluid through the capillary tube remains constant.

The process of the invention for quantitatively determining the nitrogen or other elemental content in a material sample begins with obtaining a weighed amount of the material to be tested. A very useful amount of a solid sample when using a 100 ml. digestion flask is 0.25 grams. If the material to be tested is a solid, the sample should be dry and preferably is finely divided. When the sample to be tested is a liquid, it is preferred to use about 1–5 grams of sample because it is easier to measure and handle.

The weighed sample is placed into the volumetric flask, after which concentrated sulfuric acid is added. Generally the amount of sulfuric acid added is approximately two to three milliliters when the sample weight is 0.25 grams and the sample is a carbohydrate. More acid is normally used when the sample contains considerable carbon-hydrogen compounds such as are found in petroleum products, coal, and the like. The important consideration is to use a sufficient amount of acid to wet the sample so that the sample will not bake to dryness during the process. No catalysts or other agents need be added.

The flask is then placed on the platen and heated at a temperature and for a time sufficient to char the sample and bring the sulfuric acid to a boil (about 300° to 330° C.). This normally only takes about two to five minutes, depending upon the sample size, the temperature to which it is heated, the type of material in the sample, etc. Then there is continuously added to the boiling digestion mixture in the flask a reagent solution, i.e. mixture, of sulfuric acid and hydrogen peroxide. That is, the reagent is added as a sustained constant flow at a particular rate, while the digest is boiling. It is important to add the reagent in such a manner that the digest remains at or near the boiling temperature and that explosive decomposition or vaporization of the peroxide reagent is avoided. If the reagent was simply added dropwise onto the top surface of the digest there would be explosive decomposition; it has been noted that the advantages of the present technique are not obtained when the reagent is dropped directly onto the surface of the digest mixture. Rather, the advantages are only obtained when the reagent is added in a slow manner such that a slow, continuous stream is presented where the reagent meets the digest.

The simplest manner for presenting the reagent to the digest in a controlled manner is to have the reagent flow slowly down the interior surface of the flask. In this approach the amount of reagent presented per unit of time is very limited and rapid vaporization or decomposition is avoided. Because only a small amount of reagent is presented per unit of time, the digest remains at or near its boiling point and this is very desirable. The reagent solution also boils as it mixes with the digest and this is effective in causing the desired oxidation of the material sample.

By adding the reagent solution in such a continuous and controlled fashion the high temperature of the boiling digestion mixture is maintained, yet a high concentration of peroxide is built up in the digest and maintained for the duration of the oxidation. The effectiveness of the reagent is thus due to a combination of high temperature (i.e., up to about 330° C.), high concentration of peroxide, and long residence time of the peroxide in the digest.

The continuous flow addition of the peroxide reagent is such that a steady state concentration of peroxy species is maintained in the digest while the temperature of the digest is maintained at or near the boiling point of the sulfuric acid. This technique results in very rapid and effective digestion of the material sample without loss of nitrogen or other element being recovered. This technique is much more rapid and effective than prior techniques in which hydrogen peroxide was added in a series of increments or slugs.

Figure 2:
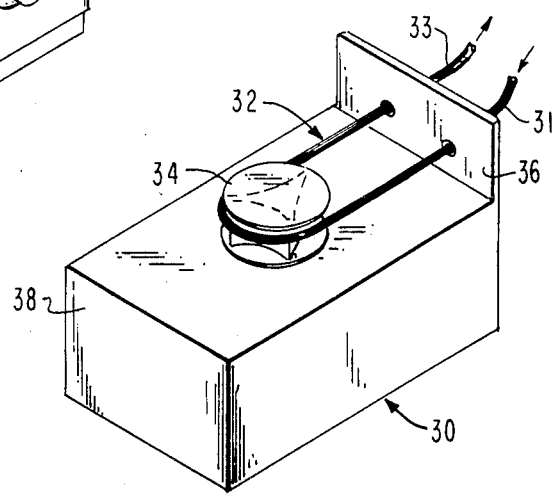
FIG. 2 shows one type of pumping device which is useful in another embodiment of the invention.

The reagent solution may be introduced into the top of funnel 29 by various means. For example, it may be simply poured into funnel 29 from a flask, graduated cylinder, etc. An alternative method for adding the reagent to the flask is to pump the reagent into a manifold not having a capillary funnel therein. In FIG. 2, for example, pumping apparatus 30 is shown which is useful for delivering the reagent to a manifold from a source container. The apparatus includes a length of flexible tubing 32 which is stretched tightly around a star wheel 34. The tube is secured in upright retention member 36, as shown. One end 31 of tube 32 is in communication with a source of the reagent while the opposite end 33 of tube 32 is operably connected to the manifold. The star wheel is rotatably driven by a motor within housing 38 at a predetermined rate. As the pointed projections of the star wheel successively squeeze tubing 32 closed, liquid from the reagent source container is moved through tube 32 and out end 33. The speed of rotation of star wheel 34 determines the rate at which the liquid is pumped through tube 32. The speed may be adjusted, as desired, to obtain a controlled addition rate of reagent (e.g., in the range of approximately 0.5 to 10 milliliters per minute, preferably 1-3 milliliters per minute).

The reagent solution used in this invention is prepared by mixing concentrated sulfuric acid with hydrogen peroxide in the range of about 2 to about 8 parts by volume of hydrogen peroxide solution (50%) to one part by volume of sulfuric acid. Preferably, one part by volume of the acid is added to four parts by volume of a 50% hydrogen peroxide solution. When the acid and the peroxide are combined as described above, some amount of peroxysulfuric acid is obtained and some portion of the peroxide remains as peroxide.

In the apparatus shown in FIG. 1, the reagent is added to the funnel 29 within manifold 24. The reagent then exits through the lower end of capillary tube 29a in a continuous manner at a constant rate and flows into funnel 27 and thence into the flask 20 along an interior surface thereof. In a typical example, when adding twenty milliliters of reagent, it takes ten minutes for it to flow through the capillary tube into the flask. After the reagent has been added, the digest is refluxed for about one minute until residual peroxide and peroxysulfuric acid are decomposed.

The required digestion time will vary, depending upon the ease with which the sample is digested. The digestion time is typically in the range of one minute or less up to about fifteen minutes for very difficult materials. This is illustrated below in connection with Tables 1 and 2. These tables show the required digestion time, and amount of reagent solution used, when testing a wide variety of samples. One may determine the minimum digestion time required for other materials not present in the tables by preparing a digestion curve. This is done by digesting several identical samples for varying periods of time and then quantitatively measuring the amount of nitrogen recovered from each sample. From plotting the results on a graph of digestion time versus percent nitrogen recovered, one will readily observe the minimum digestion time required to reach the point on the curve where the percent nitrogen recovered is at its highest level. Of course, one may simply digest the sample for about 20 minutes and be confident that essentially all of the recoverable nitrogen has been obtained or any sample.

The digestion process of the present invention is very rapid as compared to conventional techniques. This is illustrated with the following comparisons for digestion times (including a normal period of approximately 5 minutes to char the sample before reagent addition):

| Compound | Digestion Time Required | |
|---|---|---|
| | Conventional | Present Invention |
| Nicotinic acid | 180-240 minutes | 17.5 minutes |
| p-Nitroaniline | 40-50 | 8.5 |
| Tryptophan | 55-80 | 9.7 |

The speed and accuracy of the process of this invention is further illustrated in the graph of FIG. 3. This graph shows the digestion times required for nicotinic acid when using the process of this invention (curve A) and a conventional Kjeldahl process (curve B). The conventional process uses selenium and mercury catalysts, as well as potassium sulfate addition, and it is described, for example, in Analytical Chemistry, 17, pp. 437-38. These curves illustrate that the conventional process requires approximately three hours of digestion of nicotinic acid in order to obtain a nitrogen determination approaching theoretical. Using the process of this invention it is only necessary to digest for approximately fifteen minutes (after the charring of the sample) in order to obtain a nitrogen determination approaching theoretical.

After the digestion process has been completed the digest and the flask are preferably cooled (e.g., by placing the flask in warm water and then cooler water so that the flask does not break, or the flask may be air cooled). After the digest has been adequately cooled, the digest may be diluted with water to form a test solution, if desired. Because the flask is volumetric, all that is required is to fill the flask to the fill line with desired diluent such as water or other solvent.

However, it is not necessary to cool the digest or dilute it as described above in order to measure the nitrogen content. For example, a small aliquot of the digest may be removed from the digestion flask and analyzed in accordance with conventional techniques for nitrogen content. Optionally, the digest may be diluted with a solvent to form a test solution. Still other alternatives for analyzing the digest directly, without adding diluents, include distillation or use of an autotitrator.

Of course, it is also possible to analyze the digest for various elements other than nitrogen. Because no salts or catalysts were added to the digestion flask during the process of this invention, the resulting digest is suitable for quantitative analysis of various materials present therein. For example, the digest may be diluted with desired diluent and examined for elements such as nitrogen, phosphorus, potassium, manganese, calcium, magnesium, zinc, iron, copper, cobalt, or other elements.

After a test solution has been prepared as described above, it may be used in accordance with known techniques for quantitatively determining the amount of nitrogen present. A preferred technique for determining nitrogen content involves a colorimetric method known as nesslerization. Organic nitrogen present in the digest sample is converted to ammonium nitrogen. The Nessler reagent, a strongly alkaline solution of sodium or potassium mercuric iodide, is added to the digest sample and it reacts with the ammonium nitrogen to form a yellow color. The intensity of the yellow color is directly proportional to the amount of ammonium nitrogen present. Of course, other types of colorimetric procedures may be used instead.

Another method for determining the nitrogen content in the digest is known as a titrimetric method. The ammonia in the digest is distilled out and trapped in a solution which is then titrated with acid to determine the amount of ammonia present.

In yet another known technique the ammonia in the digest is determined potentiometrically. An ammonia ion selective electrode is used in operable connection with a pH/mV meter. Other conventional potentiometric methods may also be used.

In Table 1 below various different types of common organic materials are grouped accordingly to their ease of digestion in the process of the present invention. The maximum time and amount of reagent solution generally required for use in the digestion process (for 99% recovery) for each type is also listed, assuming a sample size of 0.25 gram.

TABLE 1

| Group | Sample Type | Reagent Volume (mL) | Digestion Time (minutes) |
| --- | --- | --- | --- |
| I | wheat (flour, mids), urea | 5 | 2.5 |
| II | corn (silage, meal, leaves), barley, clover, grass hays, other grain | 10 | 5 |
| III | soybean meal, meat and bone meals, mixed feeds with soy or meat bases, feather meal, dry milk | 15 | 7.5 |
| IV | fish meal, supplements with fish base, alfalfa, rice products, processed poultry litter | 20 | 10 |
| V | synthetic compounds of refractory nature, pyridine and pyridine-like structures | 30 | 15 |

In Table 2 below various specific materials within each group from Table 1 are listed in addition to the digestion time required for each in the process of this invention when using the amount of reagent stated.

TABLE 2

| Sample | Time (minutes) | mL of Reagent |
| --- | --- | --- |
| Group I | | |
| Aspartic Acid | 1.0 | 2 |
| Arginine | 1.0 | 2 |
| Wheat Mids | 2.0 | 4 |
| Whole-wheat Flour | 2.0 | 4 |
| Phenylalanine | 2.5 | 5 |
| Serine | 2.5 | 5 |
| Corn leaves | 2.5 | 5 |
| Group II | | |
| Nitroaniline | 2.7 | 6 |
| Barley | 3.5 | 7 |
| "Meow Mix" Cat Food | 3.5 | 7 |
| Sweet Clover | 4.2 | 9 |
| Corn Meal | 4.5 | 9 |
| Corn Silage | 4.5 | 9 |
| Tryptophan | 4.7 | 10 |
| Tyrosine | 4.8 | 10 |
| Acetanilide | 4.4 | 9 |
| Soybean Meal | 3.3 | 7 |
| Bovine Liver | 5.5 | 11 |
| Meat and Bone Meal | 4.9 | 10 |
| Group III | | |
| Feather Meal | 5.5 | 11 |
| Chick Feed | 6.0 | 12 |
| Methionine | 6.3 | 13 |
| Histidine | 6.5 | 13 |
| Instant Dry Milk | 6.8 | 14 |
| THAM* | 5.9 | 12 |
| Group IV | | |
| Processed Poultry Litter | 8.0 | 16 |
| Rice Products | 8.5 | 17 |
| Beef Protein Supplement | 9.0 | 18 |
| Alfalfa | 9.5 | 19 |
| Fish Meal | 10.0 | 20 |
| Pyridine | 10.0 | 20 |
| Group V | | |
| Leucine | 10.5 | 21 |
| Tetraphenylporphine | 11.9 | 24 |
| Nicotinic Acid (Niacin) | 12.5 | 25 |
| Lysine | 15.0 | 30 |

*Tris(hydroxymethyl)aminomethane

The process of the invention is not only very rapid and simple, it is extremely accurate and produces more reliable results than observed using the conventional Kjeldahl method. Furthermore, the digestion process does not contaminate the sample because no salts or catalysts are added.

The digestion process of the invention is also very useful in providing a digest which is suitable for direct aspiration in conventional atomic absorption spectroscopy methods. For example, the digestion process can be used to form a suitable digest from organic and inorganic materials such as sewages, waters, sediments, sludges, and industrial and domestic wast products. The digest can then be tested by atomic absorption spectroscopy to determine the amounts of various metals present.

As a further example illustrating the effectiveness and accuracy of the technique of this invention, nicotinic acid was digested in two different manners as follows:

(a) 0.25 gram of nicotinic acid was placed in a digestion flask along with 2 milliliters of concentrated sulfuric acid, followed by heating for five minutes at a temperature at or below 322° C. to char the sample. Then a reagent solution (one part by volume sulfuric acid and four parts by volume of 50% hydrogen peroxide solution) is added to the digestion, while the digest is boiling at a temperature at or below 322° C., in a continuous manner at the rate of 2 milliliters per minute for 12.5 minutes (i.e., a total of 25 milliliters of reagent added). Then the digest is heated for an additional minute at the same temperature, after which the digest is cooled. Then the sample is tested colorimetrically, revealing 100% recovery of nitrogen and phosphorus.

(b) 0.25 gram of nicotinic acid was placed in a digestion flask along with 2 milliliters of concentrated sulfuric acid, followed by heating for five minutes at a temperature at or below 322° C. to char the sample. Then the same reagent solution as described above was added to the digest while the digest was boiling. The reagent solution was added as rapidly as possible without allowing the digest to boil out of the flask. A total of 25 milliliters of reagent solution was added in this manner within a period of about two minutes. The digest was heated at a temperature at or below 322° C. for a period of 18.5 minutes from the time the reagent addition started. Then the digest is cooled. Testing the sample colorimetrically showed that there was only 69% recovery of nitrogen and phosphorus.

This example dramatically demonstrates that the continuous flow method of addition of hydrogen peroxide reagent provides unexpectedly accurate, rapid and effective results.

What is claimed is:

1. A process for digesting a sample of a material comprising the steps of:
   (a) placing a weighed amount of a sample of a material in a digestion flask;
   (b) adding concentrated sulfuric acid to said flask to form a digest;
   (c) heating said digest at a temperature and for a time sufficient to char said sample and bring said digest to a boil at a temperature less than about 330° C.; and
   (d) continuing to boil said digest at said temperture less than about 330° C., while simultaneously continuously adding a reagent solution to said digest, for a time sufficient to convert all nitrogen present in said sample to ammonium ions, said time being less than about 15 minutes, said reagent solution comprising hydrogen peroxide and concentrated sulfuric acid, and wherein said reagent solution enters said digest along an interior surface of said flask such that a slow continuous stream of said reagent solution is presented where said reagent solution meets said digest.

2. A process in accordance with claim 1, wherein said material is organic.

3. A process in accordance with claim 1, wherein said material is inorganic.

4. A process for the quantitative determination of the nitrogen content in a material sample, the process comprising the steps of:
(a) placing a weighed amount of a material sample in a digestion flask;
(b) adding concentrated sulfuric acid to said flask to form a digest;
(c) heating said digest at a temperature and for a time sufficient to char said material sample and bring said digest to a boil at a temperature less than about 330° C.;
(d) continuing to boil said digest at said temperature less than about 330° C., while simultaneously continuously adding a reagent solution to said digest, for a time sufficient to convert all nitrogen present in said material sample to ammonium ions, said time being less than about 15 minutes, said reagent solution comprising hydrogen peroxide and concentrated sulfuric acid, and wherein said reagent solution enters said digest along an interior surface of said flask such that a slow continuous stream of said reagent solution is presented where said reagent solution meets said digest; and
(e) quantitatively determining the nitrogen content in said material sample by quantitatively detecting ammonium ions in said digest.

5. A process in accordance with claim 4, wherein said material sample is dry and finely divided.

6. A process in accordance with claim 4, wherein said material sample is liquid.

7. A process in accordance with claim 4, wherein ammonium ions in said digest are quantitatively determined by means of titrimetric analysis.

8. A process in accordance with claim 4, wherein ammonium ions in said digest are quantitatively determined by means of potentiometric analysis.

9. A process in accordance with claim 4, wherein said digestion flask is a volumetric flask.

10. A process in accordance with claim 4, wherein said reagent solution comprises 1 part by volume of concentrated sulfuric acid and 4 parts by volume of a 50% hydrogen peroxide solution.

11. A process in accordance with claim 4, wherein said reagent solution is added to said digest by means of a capillary flow funnel.

12. A process in accordance with claim 4, wherein said reagent solution is added to said digest by means of a pump.

13. A process in accordance with claim 4, wherein said flask has an open top; and wherein a manifold is attached to the top of said flask and an aspirator is operatively connected to said manifold.

14. A process in accordance with claim 4, wherein the quantitative determination step includes cooling said digest and diluting said digest with water to form a test solution.

15. A process in accordance with claim 14, wherein the quantitative determination step also includes quantitatively determining ammonium ions in said test solution by means of colorimetric analysis.

16. A process in accordance with claim 15, wherein Nessler reagent is added to said test solution prior to colorimetric analysis.

17. A process for the quantitative determination of the nitrogen content in a material sample, the process comprising the steps of:
(a) placing a weighed amount of a material sample in a digestion flask, wherein said flask is a volumetric flask;
(b) adding concentrated sulfuric acid to said flask to form a digest;
(c) heating said digest at a temperature and for a time sufficient to char said material sample and bring said digest to a boil at a temperature less than about 330° C.;
(d) continuing to boil said digest at said temperature less than about 330° C., while simultaneously continuously adding a reagent solution to said digest, for a time sufficient to convert all nitrogen present in said material sample to ammonium ions, said time being less than about 15 minutes, said reagent solution comprising hydrogen peroxide and concentrated sulfuric acid, and wherein said reagent solution enters said digest along an interior surface of said flask such that a slow continuous stream of said reagent solution is presented where said reagent solution meets said digest;
(e) cooling said digest;
(f) diluting said digest with water to form a test solution; and
(g) quantitatively determining said nitrogen content in said material sample by quantitatively detecting ammonium ions in said test solution.

18. A process in accordance with claim 17, wherein said reagent solution comprises 1 part by volume of concentrated sulfuric acid and 4 parts by volume of a 50% hydrogen peroxide solution.

19. A process in accordance with claim 17, wherein ammonium ions in said test solution are quantitatively determined colorimetrically.

* * * * *